United States Patent [19]

Byles

[11] Patent Number: 5,065,600
[45] Date of Patent: Nov. 19, 1991

[54] TEXTILE FABRIC WITH OPPOSED ABSORBENT AND NON-ABSORBENT LAYERS AND METHOD OF FABRICATING SAME

[75] Inventor: Michael N. Byles, High Point, N.C.

[73] Assignee: Guilford Mills, Inc., Greensboro, N.C.

[21] Appl. No.: 444,546

[22] Filed: Nov. 30, 1989

[51] Int. Cl.$^5$ .............................................. D04B 7/12
[52] U.S. Cl. ............................................ 66/193; 66/194
[58] Field of Search ..................................... 66/192–194

[56] References Cited

U.S. PATENT DOCUMENTS

| | | | |
|---|---|---|---|
| 4,397,160 | 8/1983 | Winter et al. | 66/120 |
| 4,576,075 | 1/1986 | Krawczyk | 66/194 X |
| 4,712,281 | 12/1987 | Scheller | 66/194 X |
| 4,881,383 | 11/1989 | Spillane et al. | 66/194 |

FOREIGN PATENT DOCUMENTS

| | | | |
|---|---|---|---|
| 2543714 | 3/1977 | Fed. Rep. of Germany | 66/193 |
| 59-9252 | 1/1984 | Japan | 66/193 |
| 60-155760 | 8/1985 | Japan | 66/192 |
| 1103359 | 2/1968 | United Kingdom | 66/192 |

OTHER PUBLICATIONS

Frottier-Kettenwirkautomaten Advertising Brochure (entitled "Warp Knitting Machines for Terry Towelling" KS4FBZ, KS3F), Mayer, Germany.

Article entitled "Improved KS4FBZ Terry Tricot Machine for Made-UP Terry Hand Towels" (Ketten Wirk Praxis), 3/76.

Guilford Mills, Inc., warp knitted fabric Style Nos. 7975, 8088.

Primary Examiner—Werner H. Schroeder
Assistant Examiner—John J. Calvert
Attorney, Agent, or Firm—Shefte, Pickney & Sawyer

[57] ABSTRACT

An integrally fabricated textile fabric has a relatively thick, dense liquid retaining absorbent pile layer of hydrophilic yarns and a non-absorbent napped layer of hydrophobic yarns at opposite faces of the fabric integrated with an intermediate ground yarn structure. The napped hydrophobic yarn layer serves to wick liquid to the absorbent hydrophilic yarn layer while resisting return flow leakage. The fabric is preferably fabricated on a warp knitting machine wherein a set of hydrophilic yarns are warp knitted by the bottom machine guide bar in overfed needle loops at the technical face of the fabric, a set of hydrophobic yarns are warp knitted on the top machine guide bar in needle loops and extended nappable underlaps at the technical back of the fabric, and two sets of ground yarns are warp knitted by a respective pair of middle guide bars intermediate the fabric faces.

25 Claims, 1 Drawing Sheet

TEXTILE FABRIC WITH OPPOSED ABSORBENT AND NON-ABSORBENT LAYERS AND METHOD OF FABRICATING SAME

BACKGROUND OF THE INVENTION

The present invention relates generally to textile fabrics and methods of producing such fabrics. More particularly, the present invention relates to an integrally fabricated textile fabric characterized basically by a liquid permeable non-absorbent layer at one fabric face and a liquid retaining absorbent fabric at the opposite fabric face and to a method of warp knitting such a fabric.

In the fabrication of various products ranging from athletic wear and other similar apparel items such as active wear and sportswear to such diverse items as diapers, incontinence garments, bed pads, chair pads and various other articles, it is desirable that the article have a high affinity for liquid absorption without producing an uncomfortably wet feel at the exposed liquid-receiving surface of the article. Traditional athletic garments and other active wear may be provided with a fleece or pile surface facing the wearer's body and be fabricated of cotton for this purpose. Conventional diapers, incontinence garments and pads, and like articles provide one or more relatively thick layers of a highly absorbent material, e.g., non-woven cotton batting, with a non-absorbent yet liquid-permeable barrier covering the liquid-receiving surface of the absorbent material. One common type of barrier is a surface-brushed polyester textile fabric. The layer or layers of batting or other absorbent material and the barrier are separately fabricated and subsequently attached together in a separate stitching or similar procedure. A liquid impervious backing is typically attached to cover the surface of the absorbent material opposite the barrier to prevent leakage of absorbed liquid.

Liquid absorbing articles of the aforementioned type generally perform acceptably for their intended purpose, but nevertheless suffer certain disadvantages. Athletic garments and active wear generally have relatively good absorbent qualities but nevertheless produce a wet feel when any significant amount of liquid is absorbed. With diapers and incontinence garments and pads, as mentioned, a relatively thick layer of the absorbent material must generally be utilized to provide an acceptable capacity for liquid absorption. Further, the necessity of attaching a separately fabricated barrier to the absorbent material increases the overall expense of fabrication of such articles.

SUMMARY OF THE INVENTION

It is accordingly an object of the present invention to provide an integrally fabricated textile fabric having a liquid permeable non-absorbent layer at one face of the fabric and a liquid retaining absorbent layer at the opposite face of the fabric by which liquid applied to the non-absorbent layer is wicked to and retained by the absorbent layer so that the non-absorbent layer is maintained essentially dry to the touch, whereby various embodiments of the fabric are suitable for a wide variety of end uses. It is a further object of the present invention to provide a method by which a warp knitted embodiment of such textile fabric may be produced.

Briefly summarized, the fabric of the present invention basically includes hydrophobic yarn formed in a raised surface construction predominantly at the one face of the fabric to form its non-absorbent layer, hydrophilic yarn formed in a relatively dense extended pile construction predominantly at the opposite fabric face to form its absorbent layer, and ground yarn formed in a dimensionally stable construction. Each of the hydrophilic, hydrophobic and ground yarns are intermeshed with at least one of the other for integrating the absorbent and non-absorbent layers. The raised surface construction of the hydrophobic yarn in the non-absorbent layer serves to resist leakage of absorbed liquid from the absorbent layer through the non-absorbent layer.

In preferred embodiments of the present textile fabric, a spun yarn of staple natural fibers, e.g., cotton, is utilized as the hydrophilic yarn. Optimal absorbency is achieved by utilizing a spun yarn consisting entirely of cotton fibers. The hydrophobic yarn is preferably a multifilament synthetic yarn, e.g., polyester. The ground yarn may be a multifilament synthetic yarn, a spun yarn of synthetic fibers, a spun yarn of a blend of synthetic and natural fibers, or a spun yarn of entirely natural fibers.

Preferably, the hydrophilic yarn is of a relatively low yarn count as measured according to the cotton count system, i.e., of a relatively high denier, which should be substantially higher than the denier of the hydrophobic and ground yarns, preferably more than twice the denier of the hydrophobic yarn. In preferred embodiments of the present fabric, the yarn count of the hydrophilic yarn is less than approximately ten.

Thus, the hydrophilic yarn should constitute in excess of at least approximately forty percent by weight of the fabric. In certain embodiments of the present fabric, the hydrophilic yarn constitutes greater than forty-five percent by weight of the fabric and in other embodiments exceeds fifty percent by weight of the fabric. The hydrophobic yarn, on the other hand, should constitute no greater than approximately forty percent of the fabric weight. The ground yarn should constitute no greater than approximately thirty percent of the fabric weight and, in certain embodiments, constitutes less than ten percent of the fabric weight.

The raised surface construction of the hydrophobic yarn may be achieved by either a napped construction or a pile construction. In certain embodiments, the ground yarn is predominately between the opposed fabric faces.

One preferred construction of the present fabric is by warp knitting the hydrophilic, hydrophobic and ground yarns in an at least three-bar, but preferably four-bar, construction. Basically, a set of hydrophilic yarns are warp knitted in overfed needle loops at the technical face of the fabric for forming the absorbent layer. A set of hydrophobic yarns are warp knitted in extended underlaps at the technical back of the fabric for forming the non-absorbent layer. At least one set of ground yarns are warp knitted in a dimensionally stable pattern. In certain embodiments, two sets of ground yarns are preferred. For example, a first set of ground yarns may be warp knitted in a chain stitch pattern and a second set of ground yarns may be warp knitted in a lay-in pattern intermediate the technical face and back of the fabric for restricting its walewise and weftwise stretching.

In one preferred four-bar construction of the fabric, the needle loops of the hydrophilic yarns are preferably formed in alternate wales and alternate courses of the fabric, with the hydrophilic yarns being anchored intermediate successive needle loops at a weftwise spacing therefrom for increasing the quantity of the hydrophilic yarns in the absorbent fabric layer. Each hydrophobic yarn is warp knitted intermediate each underlap in needle loops formed alternately in the alternate wales and in intermediate wales therebetween. The chain stitches of the first ground yarns are formed in the intermediate wales while the second ground yarns are laid in weftwise between spaced ones of the intermediate wales. Specifically, the hydrophilic yarns may be knitted in a 5-4, 7-7, 4-5, 2-2 stitch pattern, the hydrophobic yarns may be knitted in a 1-0, 3-4 stitch pattern, the first ground yarns may be knitted in a 0-1, 1-0 stitch pattern, and the second ground yarns may be knitted in a 5-5, 0-0 lay-in pattern.

The method of the present invention by which the above-described warp knitted fabric is produced is carried out on a warp knitting machine having at least top, middle and bottom yarn guide bars and a needle bar which supports a longitudinally extending series of needles. Basically, a set of hydrophilic yarns is warp knitted on the bottom guide bar in overfed needle loops forming an absorbent layer of the hydrophilic yarn needle loops in a relatively dense pile construction at the technical face of the fabric. Simultaneously, a set of hydrophobic yarns are warp knitted on either the middle or top guide bars in elongated underlaps forming a non-absorbent layer of the hydrophobic yarns in a raised surface construction at the technical back of the fabric. A set of ground yarns are also simultaneously warp knitted on the remaining guide bar in a dimensionally stable construction.

In one embodiment of the method, the overfed needle loops of the hydrophilic yarns are guided by the bottom guide bar to be formed on selected needles of the needle bar, while needle loops of the hydrophobic yarns are guided by the top guide bar to be formed alternately on the selected needles and on intermediate needles therebetween with the underlaps of the hydrophobic yarns extending between the hydrophobic yarn needle loops. Needle loops of the ground yarns are guided by the middle guide bar to be formed on the intermediate needles forming a layer of the ground yarn essentially intermediate the absorbent pile layer of the hydrophilic yarn and the non-absorbent layer of the hydrophobic yarn. After formation of the fabric in this manner, the underlaps of the hydrophobic yarn at the technical back of the fabric are napped sufficiently to substantially reduce the size of interstices in the non-absorbent layer of the hydrophobic yarns for resisting leakage of absorbed liquid from the absorbent layer of the hydrophilic yarns through the non-absorbent layer of the hydrophobic yarns. Preferably, the warp knitting machine includes a second middle guide bar by which a second set of ground yarns may be laid in non-stitch loops extending about spaced ones of the intermediate needles to form the fabric in a four-bar construction, the two sets of ground yarns providing dimensional stability to the fabric.

DESCRIPTION OF THE PREFERRED EMBODIMENT

Figure 1:
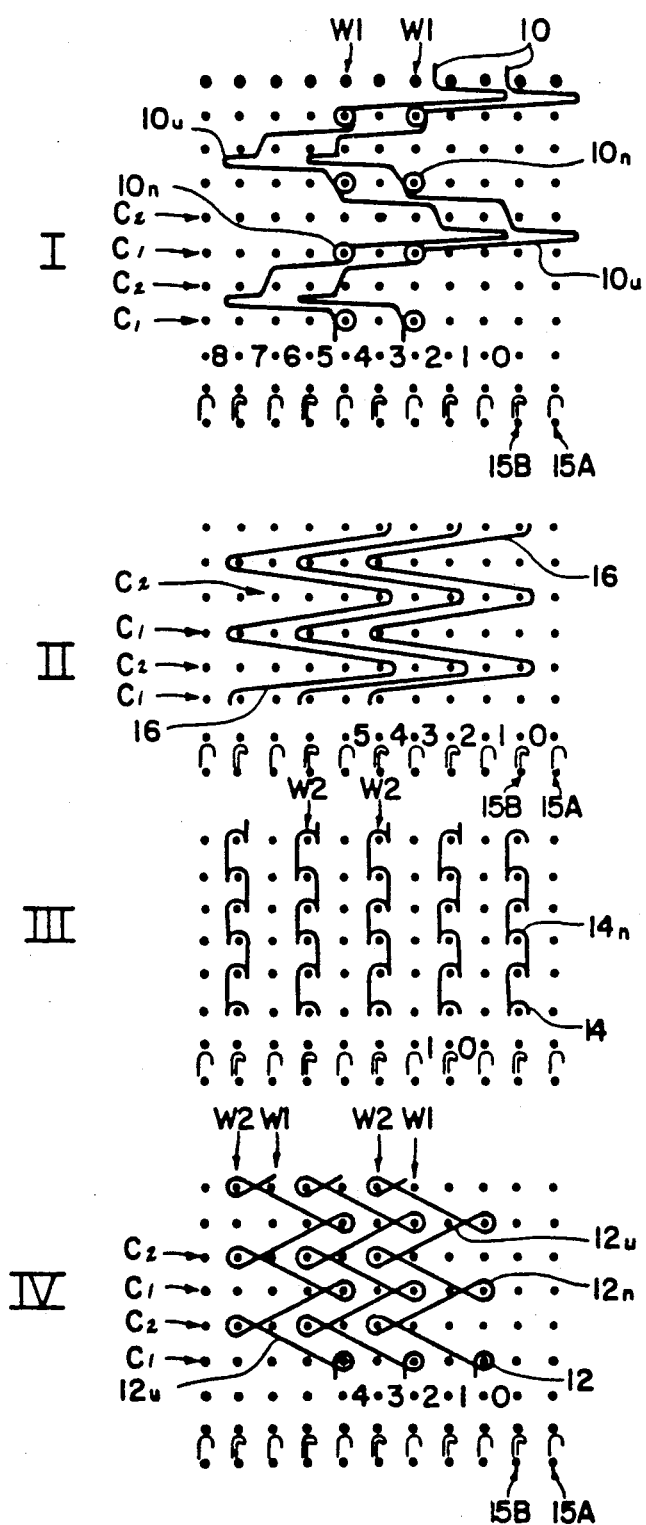
FIG. 1 is a diagram showing individually the stitch pattern for the hydrophilic, hydrophobic and ground yarns carried out by a warp knitting machine in knitting one preferred embodiment of the present fabric according to the method of the present invention.

As explained more fully herein, the preferred embodiment of the fabric of the present invention is produced, and the method of the present invention is carried out, on a warp knitting machine which may be of any conventional type of an at least three-bar construction having three or more yarn guide bars and a needle bar, e.g., a conventional tricot warp knitting machine. A four-bar warp knitting machine adapted for producing dual-faced terry toweling is preferred. One such machine is manufactured and sold by Karl Mayer Textilmaschinenfabrik GmbH, of Obertshausen, West Germany, as its Model KS4-FBZ. Another suitable warp knitting machine is manufactured by Textima of Karl-Marx-Stadt, East Germany, under the model designation Lirapol. The construction and operation of such machines are well known in the warp knitting art and need not herein be specifically described and illustrated. While the fabric of the present invention is herein illustrated and described in its preferred embodiment as a warp knitted fabric, those persons skilled in the textile fabric-producing arts will recognize that equivalent fabrics may be produced as well by weaving or circular (weft) knitting. The description and illustration herein of the preferred warp knitted embodiment of the present fabric is provided merely for illustrative purposes to provide to those persons skilled in the art an enabling disclosure of the presently contemplated best mode of producing the fabric of this invention. It is accordingly to be understood that the present invention is not to be limited to the particular embodiments herein described and illustrated.

In the following description, the yarn guide bars of the warp knitting machine are identified as "top," "middle" and "bottom" guide bars for reference purposes only and not by way of limitation. As those persons skilled in the art will understand, such terms equally identify knitting machines whose guide bars may be referred to as "front," "middle" and "back" guide bars, which machines, of course, are not to be excluded from the scope and substance of the present invention. As further used herein, the "bar construction" of a warp knitting machine refers to the number of yarn guide bars of the machine, while the "bar construction" of a warp knitted fabric refers to the number of different sets of warp yarns included in the fabric, all as is conventional terminology in the art.

Referring now to the accompanying drawings, one particular embodiment of the present textile fabric is illustrated as preferably warp knitted of a four-bar construction on a four-bar warp knitting machine according to the present method. According to this embodiment of the present fabric, the bottom guide bar of the machine is threaded on alternate guide members with a set of hydrophilic yarns 10 delivered from a warp beam (not shown), the top guide bar is similarly threaded on alternate guide members with a set of hydrophobic yarns 12 delivered from another warp beam (also not shown), the upper middle guide bar is threaded on alternate guide members with a first set of ground yarns 14 supplied from a third warp beam (also not shown), and the lower middle guide bar is threaded on alternate guide members with a second set of ground yarns 16 supplied from a fourth warp beam (also not shown).

It is contemplated that substantially any yarn having an affinity to retain water or another liquid by absorption or otherwise may be utilized as the hydrophilic yarn. In view of the widely recognized capacity of natural cotton fibers for water and liquid absorbency and further in view of the ready commercial availability of yarns spun in whole or in part of cotton fibers in a variety of yarn counts, cotton-containing spun yarns, particularly those consisting entirely of cotton fibers, are considered preferable, although those persons skilled in the art will recognize that other natural fiber yarns may function equally well.

As is well known, substantially all man-made synthetic yarns are lacking in any significant affinity for water or liquid retention and therefore are contemplated to be suitable for use as the hydrophobic yarn. It is of course preferred that the synthetic yarn selected for use as the hydrophobic yarn not be subjected to any finishing operation designed to enhance its liquid retention capability. Further, the synthetic hydrophobic yarn should have the ability to be napped by a conventional textile napping operation without destroying the structural integrity of the yarn. To provide these properties, it is preferred that a multifilament polyester yarn be utilized as the hydrophobic yarn.

Substantially any suitable conventional yarn of sufficient strength to provide structural integrity to the warp knitted fabric may be utilized as the ground yarns. For example, a spun cotton yarn or a spun yarn of cotton and synthetic fibers or a multifilament synthetic yarn may be utilized as the ground yarns. The same or different yarns may be utilized for the two sets of ground yarns.

To provide optimal liquid retaining capabilities to the fabric, it is preferred that the hydrophilic yarns constitute at least approximately forty percent of the weight of the fabric. As described more fully herein, the hydrophilic yarn may constitute in excess of forty-five percent of the fabric weight in certain embodiments and in excess of fifty percent of the fabric weight in other embodiments. The hydrophobic yarns should constitute no greater than approximately forty percent of the fabric weight, with the ground yarns supplying the balance of the fabric weight but preferably no greater than approximately thirty percent thereof. For these purposes, the hydrophilic yarn should be of a relatively low yarn count as measured according to the cotton count system (i.e., of a relatively high denier), which in each embodiment should be of a substantially higher denier than the hydrophobic and ground yarns, preferably at least twice the denier of the hydrophobic yarns. Spun cotton yarns of a yarn count of less than approximately ten are preferred.

In accompanying FIG. 1, the stitch constructions of the hydrophilic, ground and hydrophobic yarns 10,12,14,16, as carried out by the respective lateral traversing movements of the guide bars of the knitting machine according to one possible embodiment of the present fabric and method, are illustrated individually in a traditional dot or point diagram format, wherein the individual points 15 represent the needles of the needle bar of the knitting machine in the formation of several successive fabric courses C across several successive fabric wales W. As aforementioned, the Model KS4-FBZ warp knitting machine manufactured by Karl Mayer Textilmaschinenfabrik GmbH is preferred for use in producing the present fabric and performing the present method. This warp knitting machine is equipped with a longitudinal needle bar to which is mounted a longitudinally extending series of hook-type knitting needles, the hooks of alternating ones of the needles being of a substantially conventional construction defining an open yarn-receiving area within the hook while the hooks of the intervening needles define substantially smaller yarn-receiving areas so that the yarn engaging surface in each such hook is spaced farther from the outer free end of the hook than in the alternating conventional needles. This needle construction enables larger pile-type loops to be formed by the intervening needles. This needle format is described and illustrated in U.S. Pat. No. 4,397,160. In the illustrations of FIG. 1, the columns of points 15 representing the alternating conventional needles are indicated at 15A, while the columns of the points 15 representing the intervening needles with filled-in hooks are indicated at 15B.

In the illustrated embodiment of the present fabric, the bottom guide bar of the machine manipulates the hydrophilic yarns 10 to traverse laterally back and forth relative to the needle bar of the machine to stitch the hydrophilic yarns 10 on the intervening needles 15B in a repeating 5-4, 7-7, 4-5, 2-2 stitch pattern, as indicated at I of FIG. 1, while the hydrophilic yarns 10 are being fed from their respective warp beam in a conventional overfeeding fashion. Simultaneously, the top guide bar of the machine manipulates the hydrophobic yarns 12 as they are fed from their respective warp beam to traverse relative to the needle bar to stitch the hydrophobic yarns 12 in a repeating 1-0, 3-4 stitch pattern alternatingly on the needles 15A and 15B, as indicated at IV of FIG. 1. At the same time, the upper middle guide bar of the machine manipulates the first set of ground yarns 14 as they are fed from their respective warp beam to traverse relative to the needle bar to stitch the ground yarns 14 on the alternating needles 15A in a repeating 0-1, 1-0 chain stitch pattern, as indicated at III in FIG. 1. The lower middle guide bar simultaneously manipulates the second set of ground yarns 16 as they are fed from their respective warp beam to traverse relative to the needle bar to lay in the ground yarns 16 about spaced ones of the alternating needles 15A in a repeating 5-5, 0-0, non-stitch lay-in pattern, as indicated at II of FIG. 1.

As will be understood from FIG. 1, the threading arrangement of the four guide bars is set up to deliver the hydrophilic yarns 10, the ground yarns 14, and the hydrophobic yarns 12 to every alternate needle while delivering the ground yarns 16 to every intervening needle and, then, vice versa. For this purpose, guide bars having the same gauge as the needle bar, i.e., guide eyes per inch, or guide bars of one-half the gauge of the needle bar, may be utilized. In the former case, guide bars I, III, and IV would have every alternate guide eye threaded with yarn and every intervening guide eye empty, commonly referred to as one in, one out, while guide bar II would have every intervening guide eye threaded with every alternate guide eye empty, i.e., one out, one in. In the later case, each guide bar would be fully threaded.

As will thus be understood, the hydrophilic yarns 10 are interknitted with the hydrophobic yarns 12 which, in turn, are interknitted with the ground yarns 14, the ground yarns 16 being captured between the hydrophilic and ground yarns 10,14, thereby integrating the yarns in the fabric. The overfed stitch construction of the hydrophilic yarns forms the hydrophilic yarns 10 in needle loops $10n$ formed in alternating courses C1 and in alternating wales W1, each hydrophilic yarn 10 having its needle loops $10n$ formed in the alternating courses C1 and in a common wale W1 with an underlap extent 10u extending and being anchored between the successive needles loops 10n in the intervening courses C2 at a weftwise spacing from the common wale W1, thereby increasing the quantity of the hydrophilic yarn 10 in the fabric. The ground yarns 14 are formed only in the intervening wales W2, each ground yarn 14 being formed in one respective wale W2 in needle loops 14n aligned walewise with one another in every course C. The hydrophobic yarns 12 are formed in needle loops 12n formed in every alternate wale W1 in every alternate course C1 and in every intervening wale W2 in every intervening course C2, each hydrophobic yarn 12 having its needle loops 12n alternating every course between wales W1,W2 spaced apart by two intervening wales W1,W2 and in elongated underlaps 12u extending diagonally between the successive needle loops 12n in a substantially coursewise direction. In this manner, the needle loops 12n in the alternating wales W1 are interknitted in plated relationship with the overfed needle loops 10n of the hydrophilic yarn 10 in such wales and the needle loops 12n in the intervening wales W2 are interknitted with the needle loops 14n of the ground yarn 14 in such wales. By the aforementioned lay-in pattern of the ground yarns 16, the ground yarns 16 are not directly interknitted with the other yarns 10,12,14, but instead are captured and retained between the hydrophilic yarns 10 and the ground yarns 14 with each ground yarn 16 extending substantially weftwise in every course across five wales including three successive ones of the intervening wales W2 and the two successive alternate wales W1 therebetween.

Figure 2:
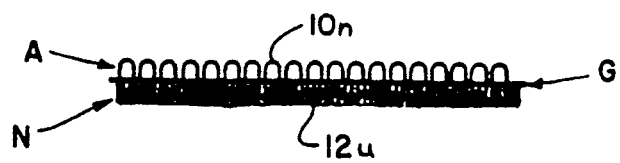
FIG. 2 is a schematic cross-sectional view of the present fabric.

In this fashion, the hydrophilic yarns 10 are structured in a terry pile construction predominantly at the technical face of the fabric whereat the needle loops 10n of the hydrophilic yarns 10 extend generally outwardly of the fabric surface, thereby forming a relatively thick and relatively dense absorbent outer layer A at the technical face of the fabric, as indicated in FIG. 2. The hydrophobic yarns 12 are formed predominantly at the technical back of the fabric whereat the extended underlaps 12u of the hydrophobic yarns 12 provide a nappable pile surface, thereby forming an outer non-absorbent layer N of the fabric at its opposite face from the absorbent layer A of hydrophobic yarns 10. The ground yarns 14,16 form a base or substrate G to the fabric predominantly between the absorbent hydrophilic yarn layer A and the non-absorbent hydrophobic yarn layer N for integrating the absorbent and non-absorbent layers and providing dimensional stability to the fabric, the walewise chain stitch construction of the ground yarns 14 restricting the walewise stretchability of the fabric while the coursewise laid-in construction of the ground yarns 16 similarly restricting the coursewise stretchability of the fabric.

Following the knitting of the present warp knitted fabric according to the present method as described, the underlaps 12u at the outer surface of the hydrophobic yarn layer are subjected to a brushing, sanding, napping or similar operation, herein broadly referred to as "napping," to produce a raised velvet-like plush surface effect at the technical back of the fabric, thereby increasing the thickness of the hydrophobic yarn layer and substantially closing or at least reducing in size the interstices formed by the stitch construction of the hydrophobic yarns 12. FIG. 2 schematically illustrates in cross-section the layered construction of the fabric as described. While napping of the hydrophobic yarn layer of the fabric is preferred in most embodiments of the present fabric, it is contemplated that napping may not be necessary in fabric embodiments wherein the hydrophobic yarn layer is of a pile construction which naturally provides an increased thickness of the hydrophobic yarn layer.

In use, the fabric of the present invention as described provides a unique and advantageous combination of properties in that the layer of the hydrophilic yarns 10 offers a relatively high capacity for liquid absorption while the non-absorbent layer of the hydrophobic yarns 12 maintains its outer surface substantially dry to the touch. Specifically, the raised nap of the underlaps 12u of the hydrophobic yarns 12 serve to direct liquid coming in contact with the non-absorbent hydrophobic fabric layer N by a wicking action through such layer and through the ground layer G to the absorbent hydrophilic yarn layer A for absorption while, at the same time, the relatively small interstices between the napped filaments of the hydrophobic yarns 12 serve to resist leakage or other return flow of any absorbed liquid from the absorbent hydrophilic yarn layer A through the non-absorbent hydrophobic yarn layer N. As a result, the plush napped hydrophobic yarn layer N remains essentially dry to the touch and comfortable even after the absorbent hydrophilic yarn layer A has absorbed and retains a relatively high liquid content. At the same time, the fabric is of a relatively small thickness in relation to its capacity for liquid absorbency, particularly as compared to conventional multi-layer absorbent battings of the like aforedescribed. As such, the fabric of the present invention is particularly adapted for use in such textile products as diapers, incontinence garments, bed and chair pads, and the like wherein a relatively high capacity for liquid absorbency is desired without the liquid-receiving surface acquiring a correspondingly wetted feel. Similarly, it is contemplated that other embodiments of the present fabric would be highly suited for various apparel items, such as athletic garments, active wear and sportswear.

As those persons skilled in the art will recognize from the foregoing disclosure, the desirable properties of the fabric of the present invention, such as the overall weight of the fabric per unit area (square yard), the percentage content by weight of the hydrophilic, hydrophobic and ground yarns, and the attendant capacity of the fabric for moisture absorbency, may be selectively modified and varied, as desired, by selection of the particular types and sizes of the constituent yarns, thereby to achieve differing embodiments of the fabric suited to differing end uses. By way of example and without limitation, the following are representative examples of fabrics according to the present invention. In each fabric, the respective stitch patterns of the hydrophilic, hydrophobic and ground yarns are as above-described.

EXAMPLE I

| Bar | Yarn | Denier (Cotton Count) | Yarn Ends/ Guide | % Weight |
|---|---|---|---|---|
| Bottom (I) | 100% Spun Cotton | 886/1 (6/1) | 1 | 45.63 |
| Lower Middle (II) | 100% Spun Cotton | 313/1 (17/1) | 1 | 18.77 |
| Upper Middle | Multi Filament | 75/40 | 1 | 4.38 |

-continued

| | Example I | | | |
|---|---|---|---|---|
| Bar | Yarn | Denier (Cotton Count) | Yarn Ends/ Guide | % Weight |
| (III) Top (IV) | Polyester Multi Filament Texturized Polyester | 168/68 | 2 | 31.22 |

EXAMPLE II

| | Example II | | | |
|---|---|---|---|---|
| Bar | Yarn | Denier (Cotton Count) | Yarn Ends/ Guide | % Weight |
| Bottom (I) | 100% Spun Cotton | 886/1 (6/1) | 1 | 54.43 |
| Lower Middle (II) | Multi Filament Polyester | 75/40 | 1 | 5.08 |
| Upper Middle (III) | Multi Filament Polyester | 75/40 | 1 | 4.32 |
| Top (IV) | Multi Filament Texturized Polyester | 168/68 | 2 | 36.17 |

EXAMPLE III

| | Example III | | | |
|---|---|---|---|---|
| Bar | Yarn | Denier (Cotton Count) | Yarn Ends/ Guide | % Weight |
| Bottom (I) | 100% Spun Cotton | 886/1 (6/1) | 1 | 54.39 |
| Lower Middle (II) | Multi Filament Polyester | 70/34 | 1 | 5.45 |
| Upper Middle (III) | Multi Filament Polyester | 70/34 | 1 | 4.36 |
| Top (IV) | Multi Filament Texturized Polyester | 168/68 | 2 | 35.80 |

EXAMPLE IV

| | Example IV | | | |
|---|---|---|---|---|
| Bar | Yarn | Denier (Cotton Count) | Yarn Ends/ Guide | % Weight |
| Bottom (I) | 100% Spun Cotton | 886/1 (6/1) | 1 | 54.02 |
| Lower Middle (II) | Multi Filament Polyester | 70/34 | 1 | 5.13 |
| Upper Middle (III) | Multi Filament Polyester | 70/34 | 1 | 4.21 |
| Top (IV) | Multi Filament Texturized Polyester | 168/68 | 2 | 36.64 |

EXAMPLE V

| | Example V | | | |
|---|---|---|---|---|
| Bar | Yarn | Denier (Cotton Count) | Yarn Ends/ Guide | % Weight |
| Bottom (I) | 100% Spun Cotton | 886/1 (6/1) | 1 | 53.15 |
| Lower Middle | Multi Filament | 70/34 | 1 | 5.02 |

-continued

| | Example V | | | |
|---|---|---|---|---|
| Bar | Yarn | Denier (Cotton Count) | Yarn Ends/ Guide | % Weight |
| (II) Upper Middle (III) | Polyester Multi Filament Polyester | 70/34 | 1 | 4.71 |
| Top (IV) | Multi Filament Texturized Polyester | 168/68 | 2 | 37.13 |

EXAMPLE VI

| | Example VI | | | |
|---|---|---|---|---|
| Bar | Yarn | Denier (Cotton Count) | Yarn Ends/ Guide | % Weight |
| Bottom (I) | 100% Spun Cotton | 886/1 (6/1) | 1 | 45.26 |
| Lower Middle (II) | Spun 50% Polyester/ 50% Cotton | 332/1 (16/1) | 1 | 19.75 |
| Upper Middle (III) | Multi Filament Polyester | 70/34 | 1 | 4.06 |
| Top (IV) | Multi Filament Texturized Polyester | 168/68 | 2 | 30.93 |

EXAMPLE VII

| | Example VII | | | |
|---|---|---|---|---|
| Bar | Yarn | Denier (Cotton Count) | Yarn Ends/ Guide | % Weight |
| Bottom (I) | Spun 50% Polyester/ 50% Cotton | 759/1 (7/1) | 1 | 50.66 |
| Lower Middle (II) | Multi Filament Polyester | 70/34 | 1 | 5.68 |
| Upper Middle (III) | Multi Filament Polyester | 70/34 | 1 | 4.74 |
| Top (IV) | Multi Filament Texturized Polyester | 168/68 | 2 | 38.92 |

EXAMPLE VIII

| | Example VIII | | | |
|---|---|---|---|---|
| Bar | Yarn | Denier (Cotton Count) | Yarn Ends/ Guide | % Weight |
| Bottom (I) | 100% Polyester "Great Feelings"* | 886/1 (6/1) | 1 | 53.87 |
| Lower Middle (II) | Multi Filament Polyester | 70/34 | 1 | 5.00 |
| Upper Middle (III) | Multi Filament Polyester | 70/34 | 1 | 4.32 |
| Top (IV) | Multi Filament Texturized Polyester | 168/68 | 2 | 36.81 |

*Trademark of E. I. DuPont de Nemours and Co., Wilmington, Delaware, for multi filament polyester yarn consisting of 50%-50% blend of 1.2 denier filaments and 2.0 denier filaments, for improved liquid retaining capacity.

EXAMPLE IX

Example IX

| Bar | Yarn | Denier (Cotton Count) | Yarn Ends/ Guide | % Weight |
|---|---|---|---|---|
| Bottom (I) | 100% Polyester "Great Feelings"* | 886/1 (6/1) | 1 | 54.14 |
| Lower Middle (II) | Multi Filament Polyester | 70/34 | 1 | 5.02 |
| Upper Middle (III) | Multi Filament Polyester | 70/34 | 1 | 4.11 |
| Top (IV) | Multi Filament Texturized Polyester | 168/68 | 2 | 36.73 |

EXAMPLE X

Example X

| Bar | Yarn | Denier (Cotton Count) | Yarn Ends/ Guide | % Weight |
|---|---|---|---|---|
| Bottom (I) | 100% Polyester "Great Feelings"* | 886/1 (6/1) | 1 | 53.15 |
| Lower Middle (II) | Multi Filament Polyester | 70/34 | 1 | 5.02 |
| Upper Middle (III) | Multi Filament Polyester | 70/34 | 1 | 4.71 |
| Top (IV) | Multi Filament Texturized Polyester | 168/68 | 2 | 37.13 |

EXAMPLE XI

Example XI

| Bar | Yarn | Denier (Cotton Count) | Yarn Ends/ Guide | % Weight |
|---|---|---|---|---|
| Bottom (I) | Spun 50% Polyester/ 50% Cotton | 759/1 (7/1) | 1 | 51.13 |
| Lower Middle (II) | Multi Filament Polyester | 70/34 | 1 | 5.67 |
| Upper Middle (III) | Multi Filament Polyester | 70/34 | 1 | 4.53 |
| Top (IV) | Multi Filament Texturized Polyester | 168/68 | 2 | 38.68 |

EXAMPLE XII

Example XII

| Bar | Yarn | Denier (Cotton Count) | Yarn Ends/ Guide | % Weight |
|---|---|---|---|---|
| Bottom (I) | Spun 50% Polyester/ 50% Cotton | 759/1 (7/1) | 1 | 50.47 |
| Lower Middle (II) | Multi Filament Polyester | 70/34 | 1 | 5.53 |
| Upper Middle (III) | Multi Filament Polyester | 70/34 | 1 | 5.22 |
| Top (IV) | Multi Filament Texturized Polyester | 168/68 | 2 | 38.78 |

EXAMPLE XIII

Example XIII

| Bar | Yarn | Denier (Cotton Count) | Yarn Ends/ Guide | % Weight |
|---|---|---|---|---|
| Bottom (I) | Spun 50% Polyester/ 50% Cotton | 759/1 (7/1) | 1 | 41.32 |
| Lower Middle (II) | Spun 50% Polyester/ 50% Cotton | 332/1 (16/1) | 1 | 21.17 |
| Upper Middle (III) | Multi Filament Polyester | 70/34 | 1 | 4.32 |
| Top (IV) | Multi Filament Texturized Polyester | 168/68 | 2 | 33.19 |

EXAMPLE XIV

Example XIV

| Bar | Yarn | Denier (Cotton Count) | Yarn Ends/ Guide | % Weight |
|---|---|---|---|---|
| Bottom (I) | Spun 50% Polyester/ 50% Cotton | 759/1 (7/1) | 1 | 40.15 |
| Lower Middle (II) | Spun 50% Polyester/ 50% Cotton | 332/1 (16/1) | 1 | 23.95 |
| Upper Middle (III) | Multi Filament Polyester | 70/34 | 1 | 4.38 |
| Top (IV) | Multi Filament Texturized Polyester | 168/68 | 2 | 31.52 |

It will also be recognized by those persons skilled in the art that the particular stitch patterns in which the hydrophilic, hydrophobic and ground yarns are knitted may also be varied provided that the ground yarns are knitted or formed about needles other than the needles which form the overfed pile needle loops of the hydrophilic yarns and provided that the stitch construction of the hydrophobic yarn provides for knitting of needle loops on both sets of needles to achieve proper integration of the respective yarns in the fabric.

Likewise, it is contemplated that embodiments of the present fabric may be of a three-bar rather than four-bar construction requiring only three sets of yarns, namely a set of hydrophilic yarns, a set of hydrophobic yarns, and only one set of ground yarns. For example, the fabric of FIG. 1 could be constructed without the ground yarns 16 and with the ground yarns 14 knitted in a non-chain stitch construction, such as 1-0, 2-3. In another embodiment of the fabric of the present invention having a three-bar construction, the hydrophilic yarns are knitted on the bottom guide bar in a repeating 3-2, 6-6 stitch pattern, the hydrophobic yarns are knitted on the middle guide bar in a repeating 5-5, 0-0 lay-in pattern, and the ground yarns are knitted on the top guide bar in a repeating 0-1, 1-0 chain stitch pattern. This fabric construction enables a relatively lightweight fabric to be produced which is suitable for apparel of the athletic, sports and active wear types. For such purposes, the hydrophilic yarn is preferably of a relatively higher cotton count, e.g., in the range of a 20/1 cotton count (denier: 266/1). Although the hydrophobic yarns are knitted on the middle bar, the chain stitch construction of the ground yarns formed on the top bar does not significantly obscure the appearance of the hydrophobic yarns at the technical back of the fabric, whereby the hydrophobic yarns are still capable of being napped to produce a non-absorbent outer fabric layer of a raised surface construction.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. An integrally fabricated textile fabric characterized by a liquid permeable non-absorbent layer at one face of said fabric adapted for initial liquid contact in use of said fabric and a liquid retaining absorbent layer at the opposite face of said fabric for wicking of liquid from said non-absorbent layer to, and retention of wicked liquid by, said absorbent layer while maintaining said non-absorbent layer essentially dry to touch, said fabric comprising hydrophobic yarn formed in a raised surface construction predominantly at said one face of said fabric to form said non-absorbent layer, hydrophilic yarn formed in a relatively dense extended pile construction predominantly at said opposite face of said fabric to form said absorbent layer, and generally inelastic ground yarn formed in a dimensionally stable generally non-stretchable construction, each of said hydrophobic, hydrophilic and ground yarns being intermeshed with at least one of the other for integrating said absorbent and non-absorbent layers, said raised surface construction of said hydrophobic yarn in said non-absorbent layer sufficiently covering said ground and hydrophilic yarns with sufficiently small interstices in said non-absorbent layer to permit liquid permeation therethrough to said absorbent layer while serving to resist leakage of absorbed liquid from said absorbent layer through said non-absorbent layer.

2. The textile fabric according to claim 1 and characterized further in that said hydrophilic yarn is a spun yarn of staple natural fibers.

3. The textile fabric according to claim 2 and characterized further in that said natural fibers are cotton.

4. The textile fabric according to claim 3 and characterized further in that said spun yarn consists entirely of cotton fibers.

5. The textile fabric according to claim 1 and characterized further in that said hydrophobic yarn comprises a multifilament synthetic yarn.

6. The textile fabric according to claim 5 and characterized further in that said filaments of said synthetic yarn are polyester.

7. The textile fabric according to claim 1 and characterized further in that said ground yarn comprises at least one of synthetic fibers and filaments and natural fibers.

8. The textile fabric according to claim 1 and characterized further in that said hydrophilic yarn is of a relatively low yarn count according to the cotton count system.

9. The textile fabric according to claim 8 and characterized further in that said hydrophilic yarn is of a yarn count of less than approximately 10.

10. The textile fabric according to claim 8 and characterized further in that said hydrophilic yarn is of a substantially higher denier than said hydrophobic and ground yarns.

11. The textile fabric according to claim 10 and characterized further in that said hydrophilic yarn is of a denier in excess of at least approximately twice the denier of said hydrophobic yarn.

12. The textile fabric according to claim 8 and characterized further in that said hydrophilic yarn comprises in excess of at least approximately 40 percent by weight of said fabric.

13. The textile fabric according to claim 12 and characterized further in that said hydrophilic yarn comprises in excess of approximately 45 percent by weight of said fabric.

14. The textile fabric according to claim 13 and characterized further in that said hydrophilic yarn comprises in excess of approximately 50 percent by weight of said fabric.

15. The textile fabric according to claim 12 and characterized further in that said hydrophobic yarn comprises no greater than approximately 40 percent by weight of said fabric.

16. The textile fabric according to claim 15 and characterized further in that said ground yarn comprises no greater than approximately 30 percent by weight of said fabric.

17. The textile fabric according to claim 1 and characterized further in that said raised surface construction of said hydrophobic yarn is a napped construction.

18. The textile fabric according to claim 1 and characterized further in that said ground yarn is predominantly between said faces of said fabric.

19. The textile fabric according to claim 1 and characterized further in that said fabric is warp knitted of an at least three-bar construction.

20. The textile fabric according to claim 19 and characterized further in that said hydrophilic yarn comprises a set of yarns warp knitted in overfed needle loops at the technical face of said fabric for forming said absorbent layer.

21. The textile fabric according to claim 20 and characterized further in that said hydrophilic yarns are anchored intermediate successive needle loops at a weftwise spacing therefrom for increased quantity of said hydrophilic yarns in said absorbent layer of said fabric.

22. The textile fabric according to claim 20 and characterized further in that said hydrophobic yarn comprises a set of yarns warp knitted in extended nappable underlaps at the technical back of said fabric for forming said non-absorbent layer.

23. The textile fabric according to claim 22 and characterized further in that said fabric is of a four-bar construction, said ground yarn including a first set of yarns warp knitted in a chain stitch pattern and a second set of yarns warp knitted in a lay-in pattern for restricting walewise and weftwise stretching of said fabric.

24. The textile fabric according to claim 23 and characterized further in that said needle loops of said hydrophilic yarns are formed in alternate wales and alternate courses of said fabric, each said hydrophobic yarn is warp knitted intermediate each said underlap in needle loops formed alternately in said alternate wales and in intermediate wales therebetween, and said first ground yarns are formed in said intermediate wales.

25. The textile fabric according to claim 23 and characterized further in that said hydrophilic yarns are warp knitted in a 5-4, 7-7, 4-5, 2-2 stitch pattern, said hydrophobic yarns are warp knitted in a 1-0, 3-4 stitch pattern, said first ground yarns are warp knitted in a 0-1, 1-0 stitch pattern, and said second ground yarns are warp knitted in a 5-5, 0-0 lay-in pattern.

* * * * *